United States Patent [19]
Zatarga

[11] Patent Number: 5,769,214
[45] Date of Patent: *Jun. 23, 1998

[54] SUTURE PACK

[75] Inventor: Catherine Zatarga, Fall River, Mass.

[73] Assignee: Deknatel Technology Corporation, Wilmington, Del.

[ * ] Notice: The portion of the term of this patent subsequent to Mar. 20, 2015, has been disclaimed.

[21] Appl. No.: 731,907

[22] Filed: Oct. 22, 1996

Related U.S. Application Data

[63] Continuation of Ser. No. 406,560, Mar. 20, 1995, Pat. No. 5,582,288.

[51] Int. Cl.$^6$ .................................................. A61B 17/06
[52] U.S. Cl. .......................................... 206/63.3; 206/339
[58] Field of Search .................................. 206/63.3, 380, 206/382, 383, 339; 53/430

[56] References Cited

U.S. PATENT DOCUMENTS 4,034,850  7/1977  Mandel et al. .
4,120,395  10/1978 Mandel et al. .
4,135,623  1/1979  Thyen .
4,253,563  3/1981  Komarnycky .
4,391,365  7/1983  Batchelor .
4,483,437  11/1984 Cerwin et al. .
4,572,362  2/1986  Kronfeld .
4,615,435  10/1986 Alpern et al. .
4,896,767  1/1990  Pinheiro .
5,024,322  6/1991  Hozwarth .
5,123,528  6/1992  Brown et al. .
5,199,561  4/1993  Roshdy et al. .
5,279,411  1/1994  Bruken .
5,582,288  12/1996 Zatarga .................................. 203/63.3

Primary Examiner—Ted Kavanaugh
Attorney, Agent, or Firm—Fish & Richardson P.C.

[57] ABSTRACT

The invention features a suture pack including a suture having needles at its ends and a pledget between the ends. The suture can be removed from the pack by pulling on one of the needles without becoming tangled on itself or on other sutures that preferably also are included in the pack. The suture package includes a support having a first retainer holding one of the needles, a second retainer holding the other needle, and a third retainer holding the pledget separately from either of the needles. The first retainer is positioned above the second and third retainers and the third retainer is offset horizontally from the second retainer. The support may also include a fourth retainer, positioned below the second retainer for holding the suture. Preferably the first, second and fourth retainers are vertically aligned.

3 Claims, 1 Drawing Sheet

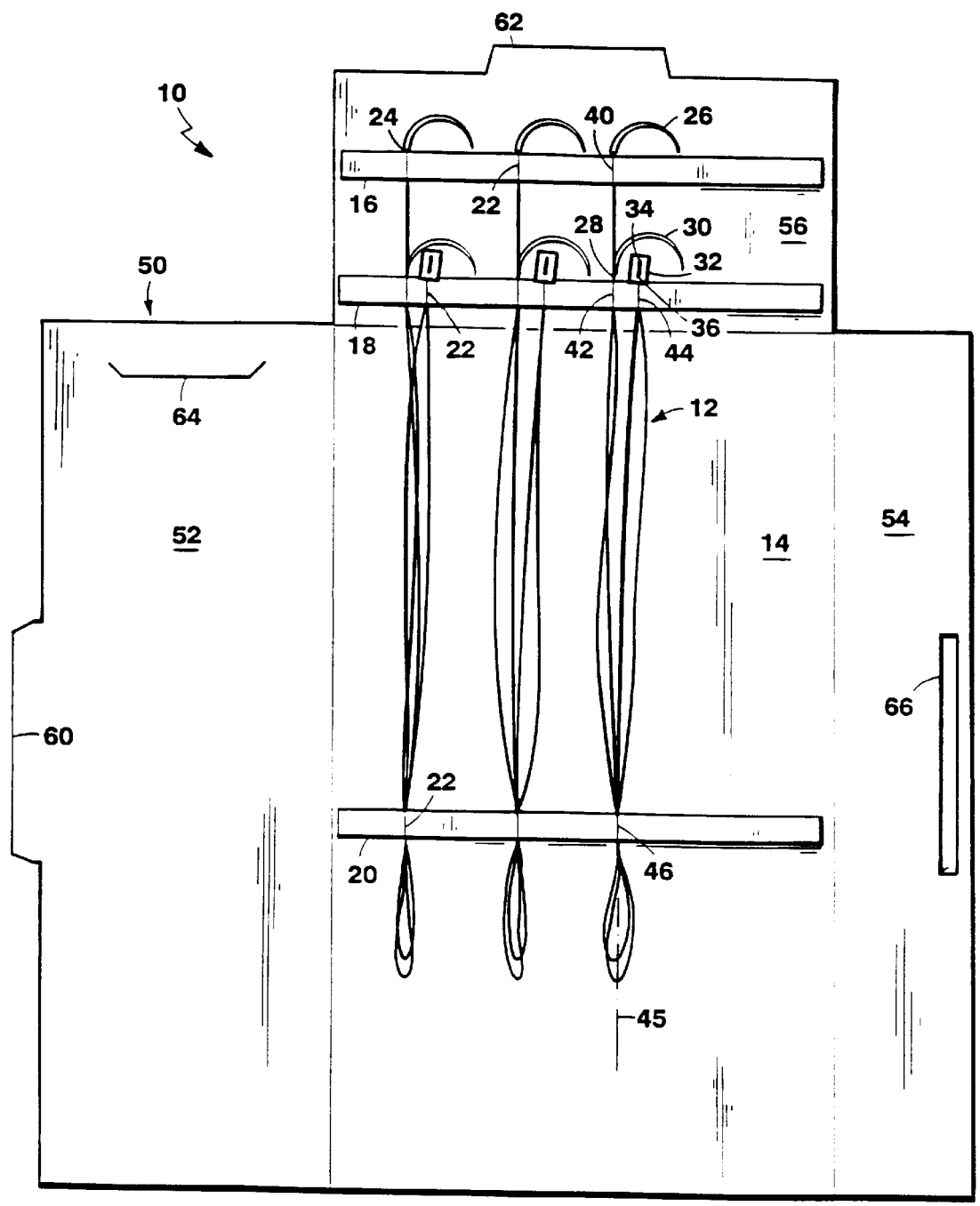
FIGURE

SUTURE PACK

This is a continuation of application Ser. No. 08/406,560, filed Mar. 20, 1995 now U.S. Pat. No. 5,582,288.

BACKGROUND OF THE INVENTION

The invention relates to suture packs.

Sutures are threads that can be used to sew the human body. One type of suture commonly used in surgery has needles at each end and a pledget. A suture having an implantable pledget can be used when suturing weak tissue to buttress the tissue and prevent the suture from cutting the tissue. Examples of instances where a suture having a pledget can be used are in mechanical valve suturing and vascular graft suturing. Such sutures typically are made in pre-determined length and included in suture packages. During surgery, a physician or an assistant removes a suture from the package by pulling on one of the needles. Of course, it is desirable that during removal from the package the suture does not become tangled either with itself or with another suture in the package.

SUMMARY OF THE INVENTION

The invention features a suture pack including a suture having needles at its ends and a pledget between the ends. The suture can be removed from the pack by pulling on one of the needles without becoming tangled on itself or on other sutures that preferably also are included in the pack. The suture package includes a support having a first retainer holding one of the needles, a second retainer holding the other needle, and a third retainer holding the pledget separately from either of the needles.

Preferably, the first retainer is positioned above the second and third retainers and the third retainer is offset horizontally from the second retainer. The support may also include a fourth retainer, positioned below the second retainer for holding the suture. Preferably the first, second and fourth retainers are vertically aligned.

The package also preferably includes a central mounting strip including the second and third retainers, an upper mounting strip including the first retainer, and a lower mounting strip including the fourth retainer. Preferably the upper mounting strip is mounted near the top of the support, allowing a physician or other user easy access to a needle to pull to remove a suture. Preferably the package also includes a cover attached to the support, that can fold over and thus enclose all or part of the sutures in the pack.

The suture packs of the invention are inexpensive and simple to construct. They can be designed to accommodate sutures intended for a wide variety of medical applications. Sutures can be removed from the preferred packs with a minimum of handling, thus decreasing the risk of contamination. Additionally, the sutures can be removed from the pack without tangling. The pledget of the suture is advantageously pre-located in a preferred position on the suture negating the need for threading or (preferably) repositioning the pledget on the suture.

Other features and advantages of the invention will be apparent from the Description of the Preferred Embodiment thereof, and from the claims.

BRIEF DESCRIPTION OF THE DRAWING

The FIGURE is a diagrammatic representation of the suture pack assembly of the invention.

DESCRIPTION OF THE PREFERRED EMBODIMENT

In the FIGURE, a suture pack assembly 10 is shown for storing sutures 12. Suture pack assembly 10 includes a suture mounting panel 14 including an upper mounting strip 16, a central mounting strip 18, and a lower mounting strip 20. Each of mounting strips 16, 18 and 20 include suture receiving portions 22, e.g., in the form of slits. Mounting strips 16, 18 and 20 may be formed of any suitable material, e.g., foam, in which suture receiving portions 22 can be formed.

Sutures 12, e.g., braided polyester fibers, braided polyester fibers with a coating of polytetrafloroethylene (PTFE) (Polydek® and Tevdek®), or polypropylene monofilament (Deklene®), are assembled in mounting panel 14 such that a first end 24 of suture 12 terminating in a hook 26 is received by a first slit 40 located in upper mounting strip 16 and a second end 28 of suture 12 terminating in a hook 30 is received by a second slit 42 located in central mounting strip 18. A pledget 32, including holes 34 and 36 for slidable mounting on suture 12, is located at central mounting strip 18 and held separately from hooks 26, 30 by a third slit 44 offset about 4 mm from slit 42. Pledget 32 has dimensions of about 3 mm×6 mm×1.6 mm, and may be formed from a variety of materials, e.g., felted PTFE. The function of pledget 32 is described below.

From first end 24 at slit 40, suture 12 runs through slit 42 to a fourth slit 46 located in lower mounting strip 20. Slits 40, 42 and 46 are substantially vertically aligned along an axis 45. The suture passes through slit 46 and then loops back again through slit 46 and extends to slit 44 located in central mounting strip 18. The suture passes through slit 44 and loops back again through slit 44. Pledget 32 is located on suture 12 along the loop at slit 44. In this position, pledget 32 acts to prevent the suture from sliding out of slit 44.

From slit 44, suture 12 runs back through slit 46 where it again loops to run through slit 46 and terminate with second end 28 of suture 12 received by slit 42. This configuration results in hooks 26 and 30 being in a tiered configuration on mounting panel 14 with pledget 32 offset from hook 30 enabling no-tangle removal of suture 12 from mounting panel 14.

The location of central mounting strip 18 on mounting panel 14 is governed by the length of sutures 12. In one embodiment in which the length of sutures 12 is about 80 cm, the distance between central mounting strip 18 and upper mounting strip 16 is about one sixth the distance between lower mounting strip 20 and upper mounting strip 16.

The suture pack assembly 10 includes a covering member 50 to enclose sutures 12. Covering member 50 includes three side panels 52, 54 and 56 constructed to fold over mounting panel 14 to enclose sutures 12. Side panels 52, 54 and 56 include tabs 60, 62 and slots 64, 66 to secure the side panels in place.

In use, when removing a suture from suture pack assembly 10, the physician or other user pulls on hook 26 resulting in the removal of the suture from the suture pack without tangling the suture on itself or on other sutures in the pack.

Other embodiments are within the claims.

What is claimed is:

1. A suture pack, comprising:

a support, and a suture having two needles, one at each of its ends, and a pledget between the ends, said support comprising an upper mounting strip including a first retainer holding a first of said needles, a central mounting strip including a second retainer holding a second of said needles and a third retainer holding the pledget separately from either of the needles, and a lower mounting strip extending along a portion of said support and including a fourth retainer in the form of a slit.

2. A suture pack, comprising:

a support, and a suture having two needles, one at each of its ends, and a pledget between the ends, said support comprising an upper mounting strip including a first retainer holding a first of said needles, a central mounting strip including a second retainer holding a second of said needles and a third retainer holding the pledget separately from either of the needles, and a lower mounting strip extending along a portion of said support and including a fourth retainer for holding said suture, said suture pack having an inner face and an outer face, said support being located on an inner face of said suture pack such that said suture is entirely contained within said inner face.

3. The suture pack of claim 2, wherein said second and third retainers are substantially aligned along a first axis and said first, second and fourth retainers are substantially aligned along a second axis.

* * * * *